(12) United States Patent
Klang

(10) Patent No.: US 11,207,544 B2
(45) Date of Patent: *Dec. 28, 2021

(54) LIGHT-BASED VAGINAL THERAPY DEVICE

(71) Applicant: Cern Corp., Trabuco Canyon, CA (US)

(72) Inventor: Gregg A. Klang, Coto de Caza, CA (US)

(73) Assignee: CERN Corporation, Trabuco Canyon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/017,998

(22) Filed: Jun. 25, 2018

(65) Prior Publication Data

US 2018/0361170 A1 Dec. 20, 2018

Related U.S. Application Data

(63) Continuation-in-part of application No. 14/789,992, filed on Jul. 2, 2015, now Pat. No. 10,004,918.

(Continued)

(51) Int. Cl.
*A61N 5/06* (2006.01)

(52) U.S. Cl.
CPC ......... *A61N 5/0603* (2013.01); *A61N 5/0624* (2013.01); *A61N 2005/0611* (2013.01);
(Continued)

(58) Field of Classification Search
CPC combination set(s) only.
See application file for complete search history.

(56) References Cited

U.S. PATENT DOCUMENTS

2007/0142880 A1* 6/2007 Barnard ............... A61N 5/0601
607/88
2009/0319008 A1* 12/2009 Mayer .................. A61N 5/0603
607/90

(Continued)

FOREIGN PATENT DOCUMENTS

KR 20090112609 A 10/2009
TW 200841896 A 11/2008

(Continued)

OTHER PUBLICATIONS

Korean Intellectual Property Office, International Search Report for corresponding International Application No. PCT/US2018/044221, Applicant: Klang, Gregg Alan, Form PCT/ISA/210, dated Feb. 11, 2019, 4 pages.

(Continued)

*Primary Examiner* — Scott Luan
(74) *Attorney, Agent, or Firm* — William A. English; Vista IP Law Group LLP

(57) ABSTRACT

The embodiments herein provide an LED based vaginal light therapy device for a plurality of bacterial and fungal infections. The device comprises an LED body, a cervix support, a single or a plurality of LEDs, a switch, a tether, microchip and a battery. One end of the device comprises a cervix support to place the device smoothly against the cervix. A plurality of LEDs is provided over the LED body. The LED body comprises one or more LEDs and each LED emits a light having a wavelength in a therapeutic zone of light. The light emitted are in a range of blue light and/or red light. The microchip is housed within the LED body. The microchip connects a battery to the single or plurality of LED's and is further connected to the switch.

18 Claims, 13 Drawing Sheets

Related U.S. Application Data

(60) Provisional application No. 62/537,899, filed on Jul. 27, 2017, provisional application No. 62/020,874, filed on Jul. 3, 2014.

(52) U.S. Cl.
 CPC ............... *A61N 2005/0626* (2013.01); *A61N 2005/0643* (2013.01); *A61N 2005/0652* (2013.01); *A61N 2005/0663* (2013.01)

(56) References Cited

U.S. PATENT DOCUMENTS

| | | | |
|---|---|---|---|
| 2010/0305406 A1* | 12/2010 | Braun | H01C 7/006 600/202 |
| 2011/0190595 A1* | 8/2011 | Bennett | A61B 1/00016 600/301 |
| 2011/0190689 A1 | 8/2011 | Bennett et al. | |
| 2014/0267662 A1* | 9/2014 | Lampo | G06F 19/324 348/77 |
| 2017/0080249 A1* | 3/2017 | Brawn | A61C 7/08 |

FOREIGN PATENT DOCUMENTS

| | | |
|---|---|---|
| WO | 2006103678 A2 | 10/2006 |
| WO | 2014166993 A1 | 10/2014 |
| WO | 2016021753 A1 | 2/2016 |
| WO | 2017003526 A1 | 1/2017 |

OTHER PUBLICATIONS

Korean Intellectual Property Office, Written Opinion for corresponding International Application No. PCT/US2018/044221, Applicant: Klang, Gregg Alan, Form PCT/ISA/237, dated Feb. 11, 2019, 6 pages.

European Patent Office, European Search Report for corresponding European Application No. 16818371, Applicant: Klang, Gregg Alan, EPO Forms 1507S, 1503, P0459, and 1703, dated Mar. 28, 2019, 7 pages.

* cited by examiner

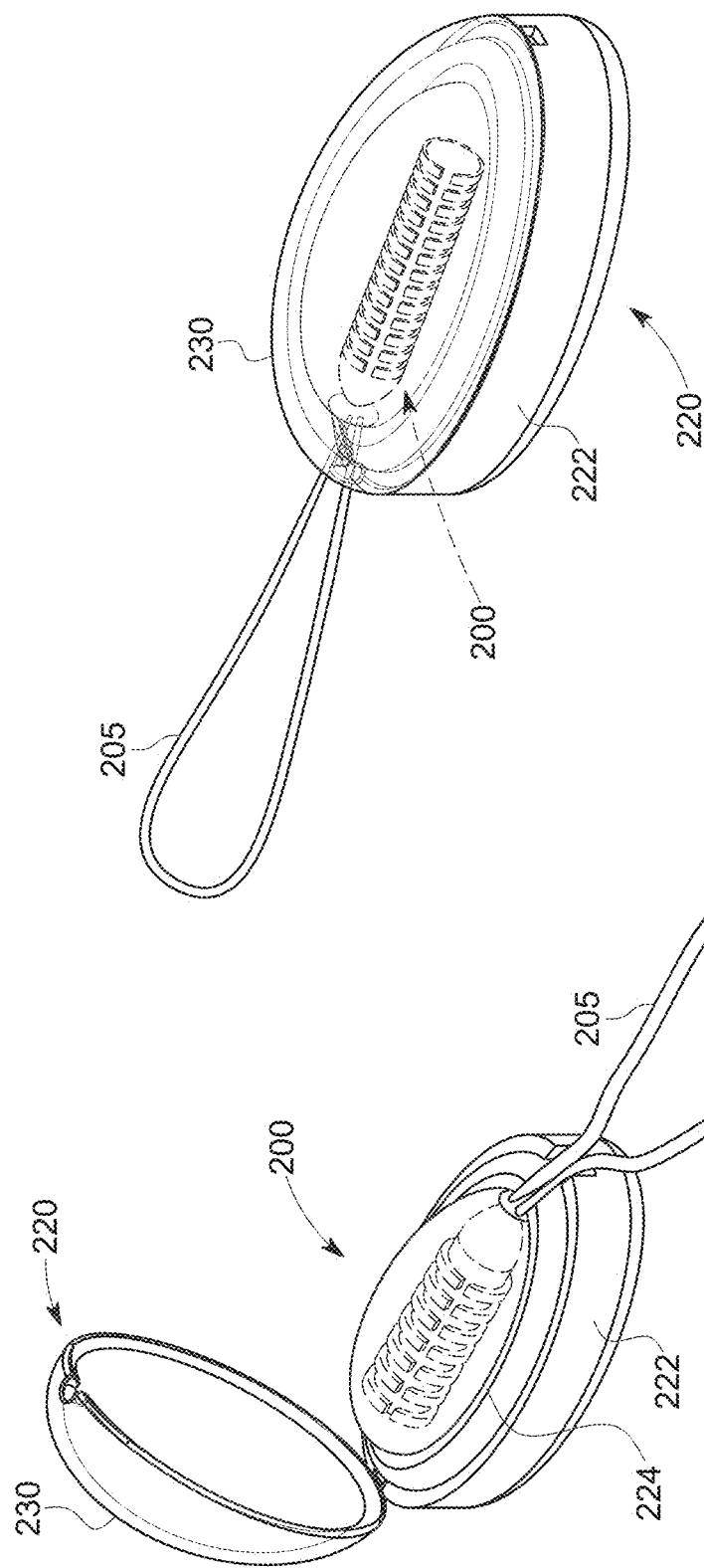

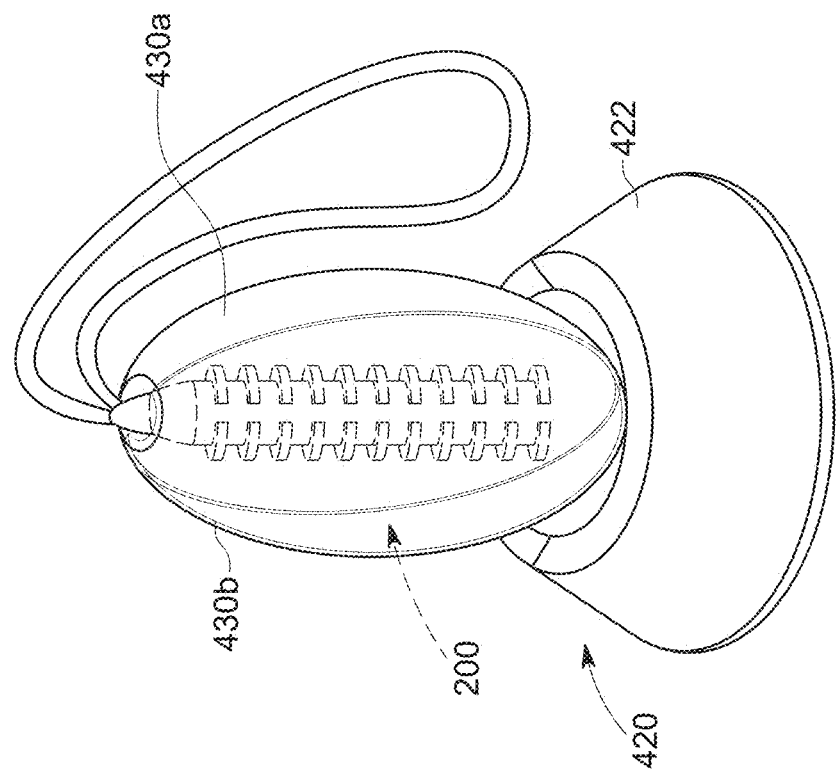
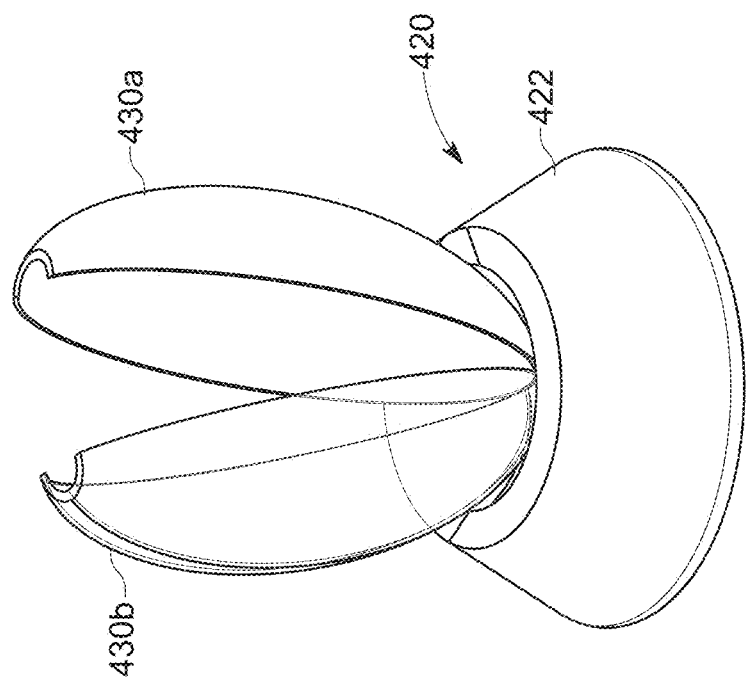

LIGHT-BASED VAGINAL THERAPY DEVICE

RELATED APPLICATION DATA

The present application claims benefit of provisional application Ser. No. 62/537,899, filed Jul. 27, 2017, and is a continuation-in-part of co-pending U.S. application Ser. No. 14/789,992, filed Jul. 2, 2015, which claims benefit of U.S. provisional application Ser. No. 62/020,874, filed Jul. 3, 2014, the entire disclosures of which are expressly incorporated by reference herein.

FIELD OF THE INVENTION

The present application generally relates to medical devices and, more particularly, to light-based vaginal light therapy devices for treatment of bacterial and fungal infections and systems and methods for using such devices.

BACKGROUND

Vaginitis is characterized by the inflammation of the vagina that results in discharge, itching and pain. The cause is usually a change in the normal balance of vaginal bacteria or an infection. Vaginitis can also result from reduced estrogen levels after menopause. In a given year as many as 75% of the woman female population experiences bacterial or fungal infection within their vagina. The symptoms range from mucus-like discharge, itching, aching, pain during intercourse to odor. The vaginal infections often have multiple causes that present challenging cases for treatment. It is critical to have a balance between naturally occurring yeast and bacteria. It is when the system is out of balance or other types of bacteria are present within the environment does one end up with vaginitis. Indeed, when one cause is treated, the other pathogens become resistant or get mutated when treated with anti-biotic and become resistant to antibiotic therapies. Sometimes the reduction in good bacteria allows for a propagation of yeast, typically *Candida albicans* resulting in yeast infection. Further, either a change in pH balance or introduction of foreign bacteria in the vagina leads to infectious vaginitis. Physical factors that contribute to the development of an infection include the following: constantly wet vulva due to tight clothing, chemicals coming in contact with the vagina via scented tampons, antibiotics, birth control pills, or a diet favoring refined sugar and yeast.

Bacterial vaginosis also known as vaginal bacteriosis or *Gardnerella Vaginitis* is a disease of the vagina caused by excessive bacteria growth. Common symptoms include increased vaginal discharge that often smells fishlike. The discharge is usually white or gray in color. Burning with urination may also occur. Itching is uncommon. Occasionally there may be no symptoms. Having bacterial vaginosis increases the risk of infection by a number of other sexually transmitted infections including HIV/AIDS. It also increases the risk of early delivery among pregnant women. Bacterial vaginosis is caused by an imbalance of the naturally occurring bacteria in the vagina. Diagnosis is suspected based on the symptom and may be verified by testing the vaginal discharge and finding a higher than normal vaginal pH and large numbers of bacteria. Bacterial vaginosis is often confused with a vaginal yeast infection. Usually treatment is through the use of antibiotics. Bacterial vaginosis is the most common vaginal infection in women of reproductive age. The percentage of women affected at any given time varies between can be as high as 35%. Antibiotics, administered either orally or vaginally are effective in treatment. About 10% to 15% of people, however, do not improve with the first course of antibiotics and recurrence rates of up to 80% have been documented. Recurrence rates are increased with sexual activity with the same pre-post treatment partner and inconsistent condom use although estrogen-containing contraceptives decrease recurrence. There is evidence of an association between Bacterial vaginosis and increased rates of sexually transmitted infections such as HIV/AIDS. Bacterial vaginosis is associated with up to a six-fold increase of HIV shedding. There is also a correlation between the absence of vaginal *lactobacilli* and infection of *Neisseria gonorrhoeae* and *Chlamydia trachomatis*. Bacterial vaginosis is a risk factor for viral shedding and herpes virus type-2 infection. Bacterial vaginosis may increase the risk infection or reactivation of HPV.

*Candidiasis*, more commonly referred to as a Yeast Infection, is most commonly caused by an overgrowth of a fungus called *Candida albicans* in the vagina. Candida is yeast, a type of fungus. Yeast is always present in the vagina in small numbers, and symptoms only appear with overgrowth. Candida can multiply when an imbalance occurs, such as when the normal acidity of the vagina changes or when hormonal balance changes. Frequently occurring yeast infections may be a sign of more serious overarching health problem such as diabetes or a compromised immune system. Recurrent infections may also be due to use of antibiotic medications. Recurrent vulvovaginal *candidiasis* affects at least 75 million women annually in the U.S. About 5-8% of women experience four or more episodes per year, diagnosed as recurrent vulvovaginal candidiasis. About 75% of all pre-menopausal women develop thrush at some point in their lives. With the introduction of over-the-counter medications for home treatment of yeast infections, many women elect to self-diagnose and self-medicate, indicating that the true incidence of yeast infections annually may be significantly under-reported.

In comparison to antibacterial therapy, antifungal treatment is limited to a very small number of drug substances. Treatment for fungal infection can be topical or systemic. Topical antifungals are generally considered as first-line therapy for uncomplicated, superficial, relatively localized fungal infections due to their high efficacy and low potential for systemic adverse effects. Systemic antifungal agents are absorbed and delivered to the body through the blood stream. The oral route is usually the safest, the most economical, and the easiest route for systemic antifungal drugs.

Topical antifungal creams and suppositories have fewer side effects than oral antifungal medications because they aren't absorbed as readily, systemically by the body, and only exert a localized effect on the genital region. Antifungal pills affect the entire body, and side effects can include nausea, headaches, and abdominal pain. However, topical medications can be messy and uncomfortable, while pills are comparatively simple. Treatment using antifungal medication is ineffective in up to 20% of cases. Treatment for thrush is considered to have failed if the symptoms do not clear within 7-14 days. In addition, the incidence of resistance to antifungal agents may be increasing, with drug-resistant fungal strains becoming increasingly common causes of infection in high-risk patient groups such as HIV/AIDS patients. Accordingly, alternative antifungal strategies are being actively sought.

Severe forms of infection are hard to treat, and frequently require more aggressive and long-term therapy, as is the case with chronic, recurrent cases. Additionally, incomplete treatments often result in drug resistant infections therefore full course of therapy should be adhered to.

Although, light therapy treatment of various bacterial, fungal or viral infection is generally known, a treatment of such infections is generally achieved through chemical or drug therapies. A use of such therapies affects an internal functioning of the vagina and uterus as the chemicals used in the form of paste or gel or liquid result in unwanted chemical reactions that are harsh or result in various complications.

Oral antifungal medications carry the risk of significant side effects, and many patients are allergic to or intolerant of these drugs. Topical solutions can be messy and inconvenient. There are no existing products for the treatment of yeast infections without also requiring medication. Hence there is a need for a product that allows for the treatment of yeast and bacterial infections quickly and simply without systemic effects. With the continued and accelerating emergence of antibiotic-resistant microorganisms, there is burgeoning interest and investment in light therapy. A device that leverages this rising technology could potentially gain rapid acceptance in specific use cases as well as broader support among the general population simply wishing to avoid exposure to additional medications.

In the view of the foregoing, devices and methods for treating intravaginal infections would be useful.

SUMMARY

The present application generally relates to medical devices and, more particularly, to light-based vaginal light therapy devices for treatment of bacterial and fungal infections and systems and methods for using such devices.

In accordance with an exemplary embodiment, a device is provided for vaginal light therapy of a patient that includes a body sized for introduction into a vagina and including a proximal end and a distal end; one or more light sources carried on the body, each light source configured to emit light outwardly from the body at one or more wavelengths within a range of non-UV germicidal light; and a tether connected with the body and configured for retrieving the device from a vagina of a patient. In an exemplary embodiment, the body has an elliptical or oblong shape, e.g., including rounded proximal and/or distal ends tapering from a central region.

Optionally, the device may include an atraumatic cervix support on the distal end of the body configured for placement against a vaginal cervix, e.g., defining a concave recess or a flat surface at the distal end. In addition, the device may include a controller within the body for controlling operation of the one or more light sources and/or a switch, e.g., a pressure-activated switch, a motion-activated switch, or a capacitance sensing switch, for activating and deactivating the one or more light sources.

In one embodiment, the outer surface of the body may be substantially smooth. Alternatively, the body may include a plurality of depressions disposed on the surface, e.g., rounded concave depressions, which may facilitate applying a drug, photosensitizer based crème, and/or other agent to the outer surface before introduction.

In one embodiment, the one or more light sources may include a plurality of LEDs or other lights mounted to the body, e.g., mounted substantially flush with an outer surface of the body. In another embodiment, one or more internal light sources may be provided within the body and a plurality of lenses may be mounted substantially flush with the outer surface of the body.

The controller may operate the one or more light sources substantially continuously when activated, may automatically turn the one or more light sources off after a predetermined treatment period, and/or may pulse the one or more light sources, e.g., to repeatedly activate and deactivate the one or more light sources and/or alternate the one or more light sources between different wavelengths to enhance treatment.

In another embodiment, an accelerometer or other motion sensor may be provided within the body that is coupled to the controller instead of an external switch. For example, the controller may monitor signals from the motion sensor to identify predetermined commands, e.g., to activate or deactivate the one or more light sources, and/or direct the device through one or more operational modes. In one embodiment, a first distinct motion or set of motions may be identified by the controller to toggle the device, i.e., alternately activating and deactivating the one or more light sources, and a second distinct motion or set of motions may be identified to direct the controller to modify the activation between a menu of options. Alternatively, a distinct motion may be assigned to each desired command.

In still another embodiment, an inductive charging circuit may be provided within the body, e.g., coupled to a battery within the body, that is used to provide electrical power to the controller and/or light sources.

In accordance with another embodiment, a system is provided that includes a vaginal light therapy device and a cradle or case for storing the device when not in use. For example, the cradle may include a planar lower surface for placing the cradle on a table or other surface, and an upper surface including a cavity sized to receive the device. For example, the cavity may define a portion of the oblong shape of a body of the device such that the device may be received in the cradle in a predetermined orientation. In one embodiment, the cavity may have a flat, concave, or convex lower surface, e.g., corresponding to the shape of a cervix support surface of the body such that the device can only be received in the cradle with the cervix support surface inserted first into the cavity.

The cradle may include one or more features for interacting with the device. For example, the cradle may include an inductive charging circuit mounted adjacent the cavity for delivering energy to the charging circuit of a device placed in the cavity. An exemplary embodiment of such a charging circuit is a circuit that generates a magnetic field that activates a corresponding circuit within the device, e.g., including one or more magnets, coils, or other components, to charge a battery of the device. The charging circuit may be activated automatically when the device is placed in the cradle or may be selectively activated by the user, e.g., by actuating a switch, button, or other actuator. In one embodiment, the cradle may include a control circuit that periodically activates the charging circuit and identifies when the resulting magnetic field indicates that a device is present in the cavity. Once a device is identified, the control circuit may activate the charging circuit for a predetermined time to charge the battery.

Alternatively, the controller in the device may include a circuit component that modifies the magnetic field or otherwise communicates wirelessly to the cradle control circuit when the controller confirms that the battery has been fully charged. When the cradle control circuit detects the modified magnetic field or other communication from the device controller, the control circuit may deactivate the charging circuit.

Optionally, the cradle may include one or more features to assist and/or facilitate cleaning the device between uses. For example, one or more light sources may be provided on the cradle for cleaning the device, e.g., applying anti-germicidal light at one or more frequency ranges, e.g., ultraviolet light, or non-ultraviolet germicidal light, and/or otherwise neutralizing latent pathogens on the outer surface of the body. In one embodiment, the cradle may include a lid or other enclosure such that the device may be inserted into the cavity and the lid closed to activate the light source(s) to treat the device. For example, once the lid is closed, the light source(s) may be activated automatically for a predetermined period of time to treat the device therein. Optionally, the cradle may include a locking mechanism that automatically locks the lid once closed, e.g., until the predetermined period of time has passed to ensure that the device has been sufficiently cleaned and/or to prevent inadvertent exposure to the light transmitted by the cradle.

In accordance with yet another embodiment, a system is provided for vaginal light therapy of a patient that includes a body sized for introduction into a vagina and including a proximal end and a distal end, one or more light sources carried on the body, each light source configured to emit light outwardly from the body at one or more wavelengths within a range of non-UV germicidal light, and a tether connected with the body and configured for retrieving the device from a vagina of a patient; and a photosensitizer configured to be activated by the one or more light sources.

In accordance with still another embodiment, a system is provided for vaginal light therapy of a patient that includes a body sized for introduction into a vagina and including a proximal end and a distal end, one or more light sources carried on the body, each light source configured to emit light outwardly from the body at one or more wavelengths within a range of non-UV germicidal light, and a tether connected with the body and configured for retrieving the device from a vagina of a patient; and a testing strip for determining a type of infection suffered by a patient.

In accordance with yet another embodiment, a method is provided for vaginal light therapy of a patient that includes inserting a body entirely into a vagina such a tether extending from the body exits the vagina; and activating one or more light sources carried on the body, each light source emitting light outwardly from the body at one or more wavelengths within a range of non-UV germicidal light. After treatment, the body may be removed from the vagina, e.g., using the tether.

In another exemplary embodiment, an LED-based vaginal light therapy device is provided for treating a variety of bacterial and fungal infections. The device may include an LED body, a single LED or a plurality of LEDs, a switch, a flexible tether, a microchip or other controller, and a battery. The LED body is made up of an appropriate medical grade material, which allows the therapeutic light to be emitted. One end of the device may include a cervix support to facilitate placing the device against the cervix. In one embodiment, a plurality of LEDs may be provided over the LED body. The LED body may include at least one LED, with each LED emitting light with a wavelength in a therapeutic zone of light, e.g., in a range of blue and/or red light wavelength. The light emitted is not in the range UV wavelength.

In an exemplary embodiment, the switch is a pressure activated switch. The microchip may be housed within the LED body and may couple a battery to the single or plurality of LEDs and may be further coupled to the switch. The microchip may control the duration of light therapy and may also be used to pulse the light. A pulsing mechanism of light may be used to treat the targeted bacteria or yeast, e.g., to stress the bacteria or yeast, which may enhance the effectiveness of treatment using the device. The switch and the LEDs may draw power from the battery through the microchip. The switch may control activation as well as deactivation of the plurality of LEDs. The tether is connected to one end of the LED body and may be used for retreating and/or progressing the device.

According to one embodiment, the plurality of LEDs emit non-UV germicidal light with a wavelength ranging within blue light wavelengths and/or red light wavelengths and/or violet light wavelengths. For example, the LEDs may emit light in the range of 405 nm-470 nm, according to one embodiment herein. The LEDs emit light in the range of 620 nm-750 nm, according to another embodiment herein. The LEDs emit light in the range of 380 nm-450 nm, according to another embodiment herein. The emitted light may kill or limit propagation of various strains of bacteria and fungus.

According to another embodiment, the microchip controls the duration of light pulse in a rapid on and/or off manner.

According to one embodiment, the LED body may be formed from a medical grade plastic. In addition or alternatively, the LED body may be sealed to avoid a flow of fluids into the device.

According to one embodiment, the device is configured for single use. Alternatively, the device is reusable, e.g., after cleaning, and may be used treatment of bacterial and fungal infection multiple times or sessions. The reusable device has a washable or rinse-able LED body. The re-usable device incorporates a mini-USB cable appropriate for use as a tether and for recharging the device.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIGS. 4A and 4B are perspective views of an exemplary embodiment of a cradle with a light therapy device stored therein, showing a lid of the cradle open and closed, respectively.

FIGS. 6A and 6B are perspective view of another embodiment of a cradle showing a lid of the cradle open and closed, respectively.

DETAILED DESCRIPTION OF THE EXEMPLARY EMBODIMENTS

Figure 1A:
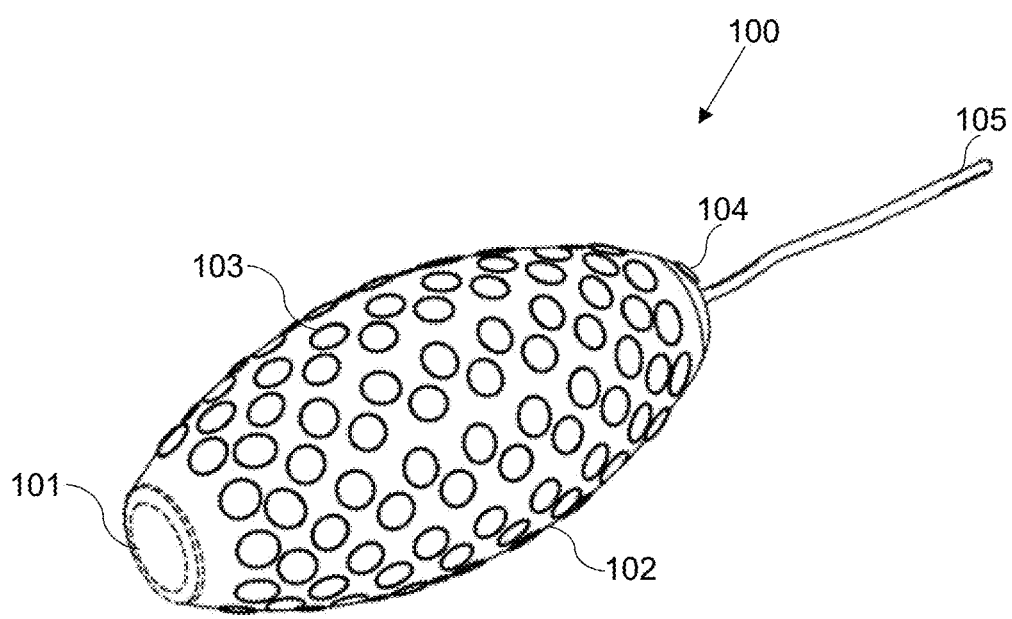
FIG. 1A illustrates a perspective view of a light-based vaginal light therapy device, according to one embodiment herein.

In the following detailed description, reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The embodiments herein provide a light-based vaginal light therapy device that may be used to treat a variety of conditions, e.g., bacterial and fungal infections, chlamydia, and the like. Alternatively, the devices and systems herein may also be useful for applying other forms of energy to the vaginal wall, e.g., to tighten adjacent tissues. In an exemplary embodiment, the device may include a body or housing, a single or a plurality of light sources, a switch, a flexible tether, a microchip or other controller, and a battery or other power source. The body is made up of an appropriate medical grade material which allows the therapeutic light to be emitted. Optionally, one end of the device may include a cervix support to place the device against the cervix. In an exemplary embodiment, the light source(s) may include a single or multiple LEDs provided over the LED body, e.g., mounted to the outer surface, within recesses in the outer surface, and the like, e.g., to provide a substantially smooth and/or atraumatic outer surface for the device. Alternatively, other internal light sources may be provided that may transmit light from the body, e.g., via one or more fiber optics, lenses, through a transparent (to the transmitted light) wall of the body, and the like (not shown). For example, the body may be formed entirely of transparent material or desired regions may be transparent such that one or more LEDs within the body may transmit light through the transparent material to treat adjacent tissue.

Each LED may emit a light with a wavelength in a therapeutic zone of light in a range of blue and/or red light or violet light (e.g., germicidal non UV) wavelength. The light emitted is not in the range UV wavelength. In an exemplary embodiment, the switch is a pressure activated switch. The controller is housed within the body and connects a battery to the light source(s) and is further connected to the switch. The controller may control the duration of light therapy and/or pulse the light. For example, pulsing the light may stress the targeted bacteria or yeast and/otherwise make the device more effective. The switch and the light source(s) draw power from the battery through the microchip. The switch controls an activation as well as deactivation of the light source(s).

The tether, e.g., a flexible cable, rope, cord, loop, and the like, may be connected to one end of the body and may have sufficient length to facilitate retrieving and/or progressing the device from a vagina. For example, in one embodiment, the tether may be a flexible cord including first and second ends coupled to the body, e.g., to define an enclosed loop having sufficient length to extend out of a vagina when the body is inserted entirely into the vagina, e.g., against a cervix. Alternatively, a cannula or other insertion tool (not shown) may be provided for inserting and/or retrieving the device.

According to one embodiment herein, the light source(s) may emit a non-UV germicidal light with a wavelength ranging between a blue light wavelength and/or a red light wavelength or a Violet light wavelength. For example, LEDs may be used that emit light in the range of 405 nm-470 nm, according to one embodiment herein. Alternatively, the LEDs emit light in the range of 620 nm-750 nm, or the LEDs may emit light in the range of 380 nm-450 nm. The emitted light may kill or limit propagation of various strains of bacteria and fungus.

According to one embodiment herein, the controller controls the duration of light pulses in a rapid on and/or off manner. For example, once activated, the controller may maintain the light source(s) active for a predetermined time period, e.g., an hour or more, and then automatically deactivate the light source(s). Optionally, when the device is activated, the controller may pulse the light source(s), e.g., rapidly turning the light source(s) off and on multiple times per minute or per second. In addition or alternatively, the light source(s) may be pulsed between different wavelengths.

According to one embodiment herein, the hardened material forming the body is a medical grade plastic.

According to one embodiment herein, the body is sealed to avoid a flow of vaginal fluid into the device.

According to one embodiment herein, the device is non-reusable in nature and serves a treatment of bacterial and fungal infection for single use. Further, the device is reusable in nature and serves a treatment of bacterial and fungal infection for multiple times by using a mini-USB cable as a tether and for recharging the device, according to another embodiment herein. The reusable device has a washable or rinse-able body.

Figure 1B:
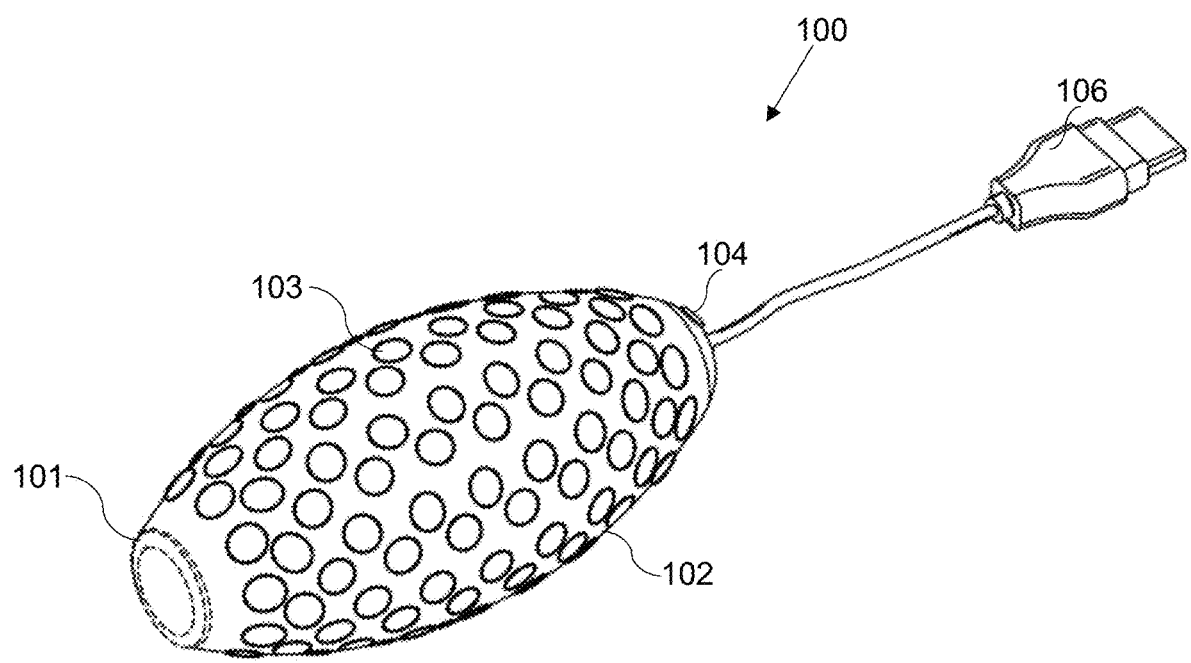
FIG. 1B illustrates a perspective view of a light-based vaginal light therapy device with a USB cord, according to one embodiment herein.
Figure 1C:
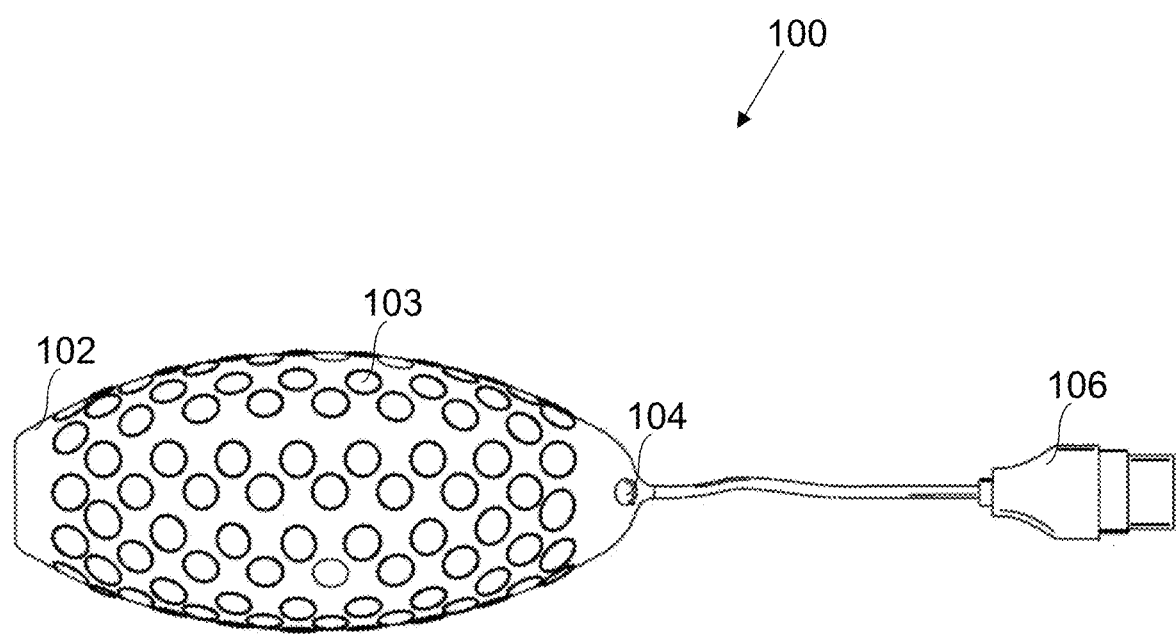
FIGS. 1C, 1D, and 1E are top, side, and front views, respectively, of the device of FIG. 1B.
Figure 1D:
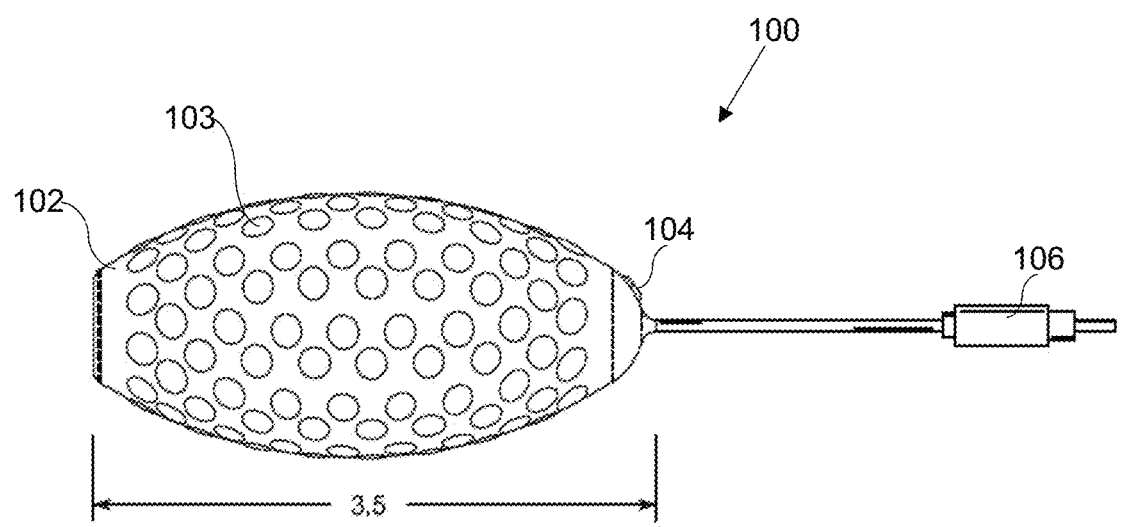
Figure 1E:
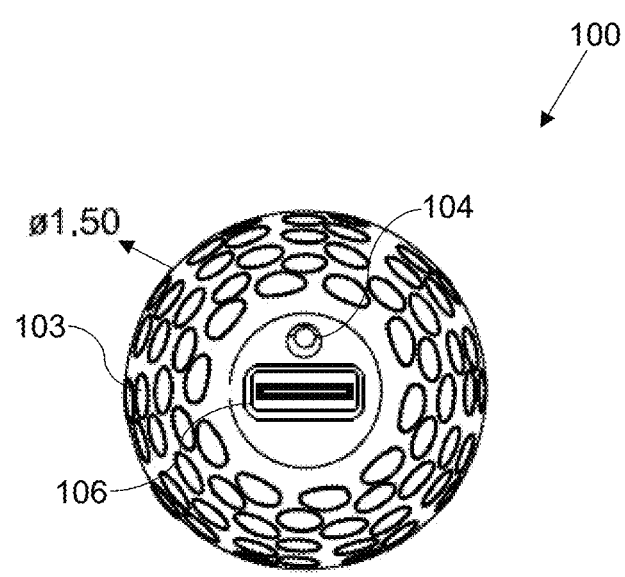
Figure 1F:
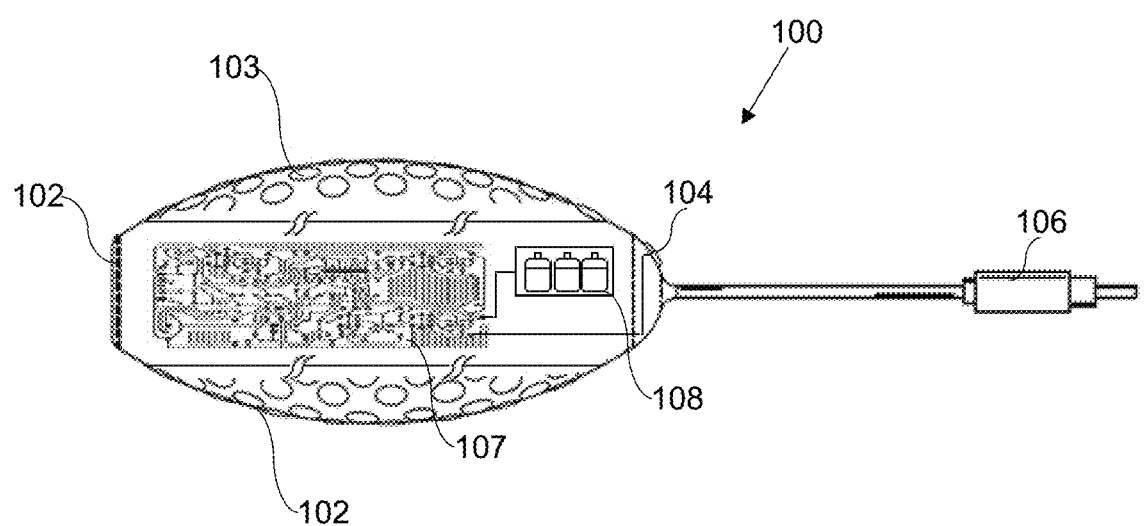
FIG. 1F illustrates a sectional view of the light-based vaginal light therapy device of FIG. 1B.

Turning to the drawings, FIG. 1A illustrates a perspective view of an exemplary embodiment of a LED-based vaginal light therapy device 100 including a body 102 carrying a plurality of light sources 103. FIG. 1B illustrates a perspective view of the LED-based vaginal light therapy device 100 with a USB cord 106, according to one embodiment herein. FIGS. 1C-1F illustrates a top view, a side view, a front view and a sectional view respectively of the LED-based vaginal light therapy device 100, according to one embodiment herein. With respect to FIGS. 1A-1F, the body 102 of the light therapy device 100 is primarily a plastic framework which allows positioning of single or multiple LEDs 103 on an external surface. As shown in FIG. 1F, a battery 108, controller 107, and/or additional electronic controllers and circuits are positioned internally with respect to the LEDs 103.

A switch 104 may be located on the outer surface of the body 102, which may be actuated by the user to activate the device 100, e.g., before insertion into the vagina. Alternatively, the tether 105 may be coupled to a switch within the body such that the tether 105 may be pulled or otherwise manipulated to activate/deactivate the light sources 104. In a further alternative, a pressure-activated switch (not shown) may be provided within the body 102 that is responsive to compressive pressures on the body 102, e.g., such that the device 100 may automatically activated once inserted into the vagina and the pressure from the surrounding muscles compress the body 102.

The device 100, once assembled, is encased into an appropriate medical grade plastic housing which is completely sealed until not serviceable. A suitable tether 105, as shown in FIG. 1A, or a mini-USB cable 106, as shown in FIG. 1B, may be attached at a first or proximal end of the body 102 to assist in insertion and/or retrieval of the device 100 inwards or outwards of the vaginal canal. Optionally, a second or distal end of the device 100 may include a cervix support 101, e.g., a concave or otherwise shaped recess to place the device smoothly against the cervix.

In an exemplary embodiment, the length and diameter of the body may be sized for insertion fully into a vagina, e.g., having an elliptical or oblong shape, i.e., with the length greater than the diameter. For example, the body 100 may have a length not more than about 3.5 inches and a maximum diameter, e.g., at a central region of the body 100, of not more than about 1.5 inches. Optionally, the body 100 may be available in multiple sizes, e.g., lengths and/or diameters, which may be provided to individual patients based on their individual anatomy. Thus, the device may have any appropriate size so as to address the size of the cavity in which it is inserted, e.g., to seat the device against the cervix and/or otherwise minimize migration during use. The surface of the body 102 is either rigid or squeezable depending on the basis of user preference and area of usage. In an exemplary embodiment, the body 100 has an ellipsoid shape, e.g., including a rounded proximal end, a distal end, a relatively large diameter central region substantially midway between the proximal end and the distal end, a proximal tapered region tapering from the central region to the proximal end, and a distal tapered region tapering from the central region to the distal end.

Figure 2:
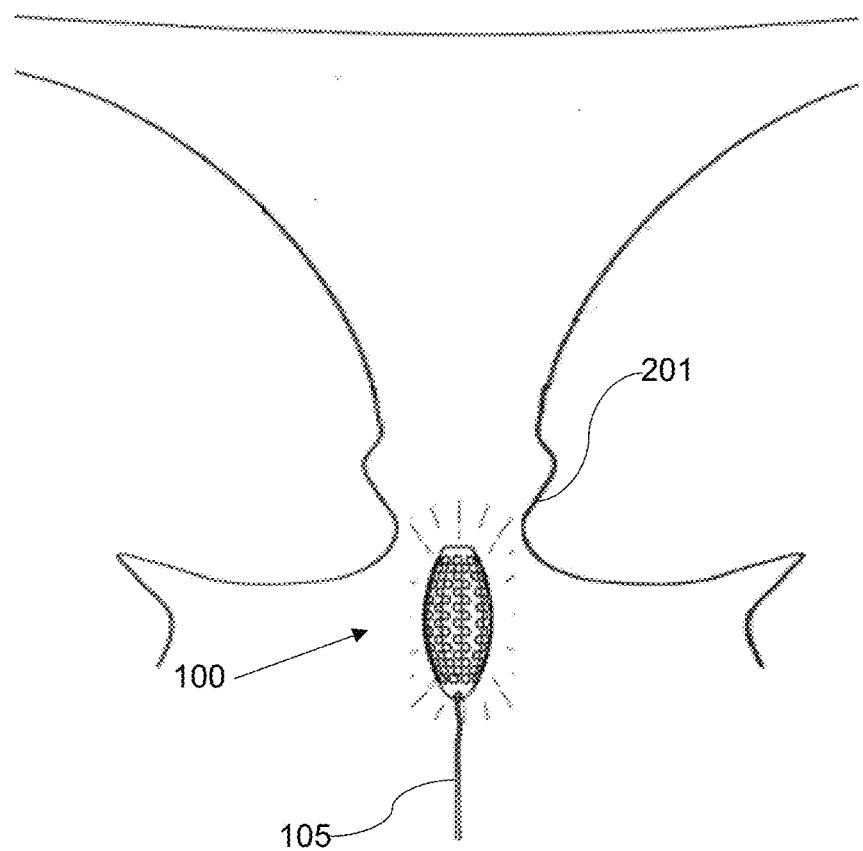
FIG. 2 illustrates placement of a vaginal light therapy device inside a vaginal canal of a female, according to one embodiment herein.

FIG. 2 illustrates a placement of the vaginal light therapy device inside the vaginal canal of a female, according to one embodiment herein. With respect to FIG. 2, the device 100 is inserted fully into the vaginal canal 201, e.g., to place the distal end against the cervix and with the proximal end receive within the vaginal canal 201, such that the tether 105 or USB cable 106 extends from the vaginal canal 201.

Figure 7:
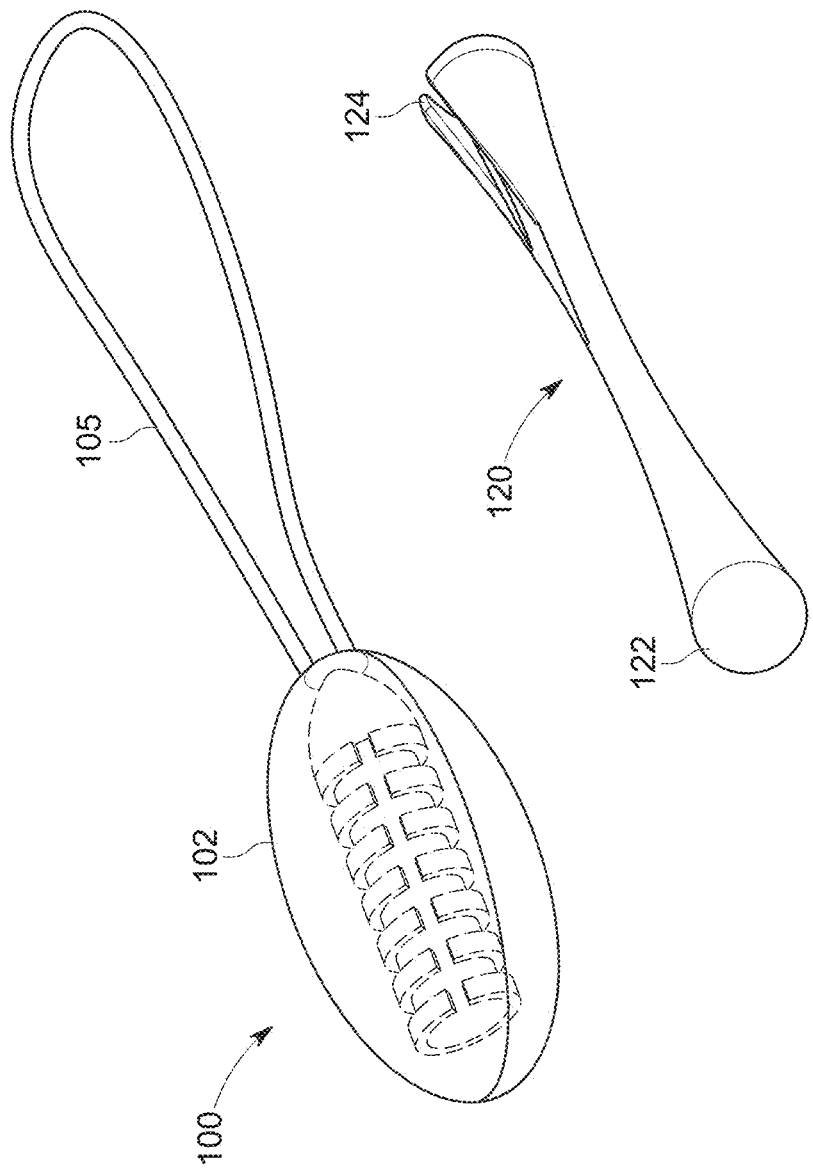
FIG. 7 is a perspective view of an insertion tool that may be provided onto which a treatment device, such as that shown in FIGS. 1A-1F, may be loaded to facilitate insertion into a user's vagina.

Optionally, as shown in FIG. 7, an insertion tool 120 may be provided to facilitate introduction of the device 100 into the vaginal canal. Generally, the insertion tool 120 includes a proximal end 122, e.g., including a handle (not shown) and/or shaped to facilitate manipulation of the insertion tool 120, and a distal end 124, e.g., including one or more connectors and/or features for releasable engaging the proximal end of the body 102. Optionally, the insertion tool 120 may include a recess, e.g., an elongated groove extending proximally from the distal end 124 sized for receiving the tether 105 of the device 100.

For example, in one embodiment, the distal end 124 may have a concave shaped recess corresponding to the shape of the body 102 such that the body may be seated partially in the recess, whereupon the tether 105 may be inserted into the groove. Optionally, the groove may provide sufficient interference fit with the tether 105 to prevent the tether from falling out and/or holding the body in place against the distal end 124. Alternatively, the insertion tool 120 may include a post, hub, or other element (not shown) over which the tether 105 may be looped or wrapped one or more times to secure the tether 105 to the insertion tool 120, e.g., with sufficient tension to hold the device 100 on the distal end 124.

In addition or alternatively, the insertion tool 120 may include one or more fingers, detents, or other features (not shown), which may be received within corresponding features in the body 102 to secure the device 100 to the distal end 124. In this embodiment, the features may be releasable, e.g., using a button or other actuator (not shown) on the proximal end 122 of the insertion tool 120 to allow the device 100 to be released once positioned within the cavity.

The insertion tool 120 may be formed from substantially rigid or malleable biocompatible material, e.g., metal, plastic, or composite material, having sufficient length to allow the distal end 124 to be inserted into the vaginal canal while holding the proximal end 122 outside the patient's body, e.g., between about five and six inches (12.5-15 cm). The insertion tool 120 may be substantially straight or may have a desired curved shape between the proximal and distal ends 122, 124 to facilitate use.

Returning to FIG. 2, before or after introduction, the device 100 may be activated, e.g., by activating an accelerometer-controlled switch, by actuating a mechanical switch 104 on the body 100 before inserting the device 100 into the vagina, and the like, as described elsewhere herein, or the device 100 may be pressure-activated, e.g., after it reaches a predetermined position in the vaginal canal 201, whereupon the light source(s) start emitting the light. The device 100 is left in the vagina for a specific period of time varying from a few minutes to hours depending upon extent of infection and kind of infection (bacterial or fungal). During the treatment period, the user may resume normal activities given the relatively small size and comfortable shape of the device 100.

The light therapy devices 100 disclosed herein may provide a harmless and/or efficient treatment of the intravaginal infection. Since the device 100 does not react with any vaginal fluid, the device 100 may be used in any patient's condition. Also the device 100 may have a relatively low cost and easy usage procedure, so it is usable even personally after a physician's approval. Optionally, one or more features of the device may be provided to address concerns such as overuse and/or overexposure. For example, the capacity of the battery may be selected to limit the maximum time period during which the device may be activated and/or to require a minimum recharge time or such parameters may be automatically controlled by the controller within the device.

Figure 3:
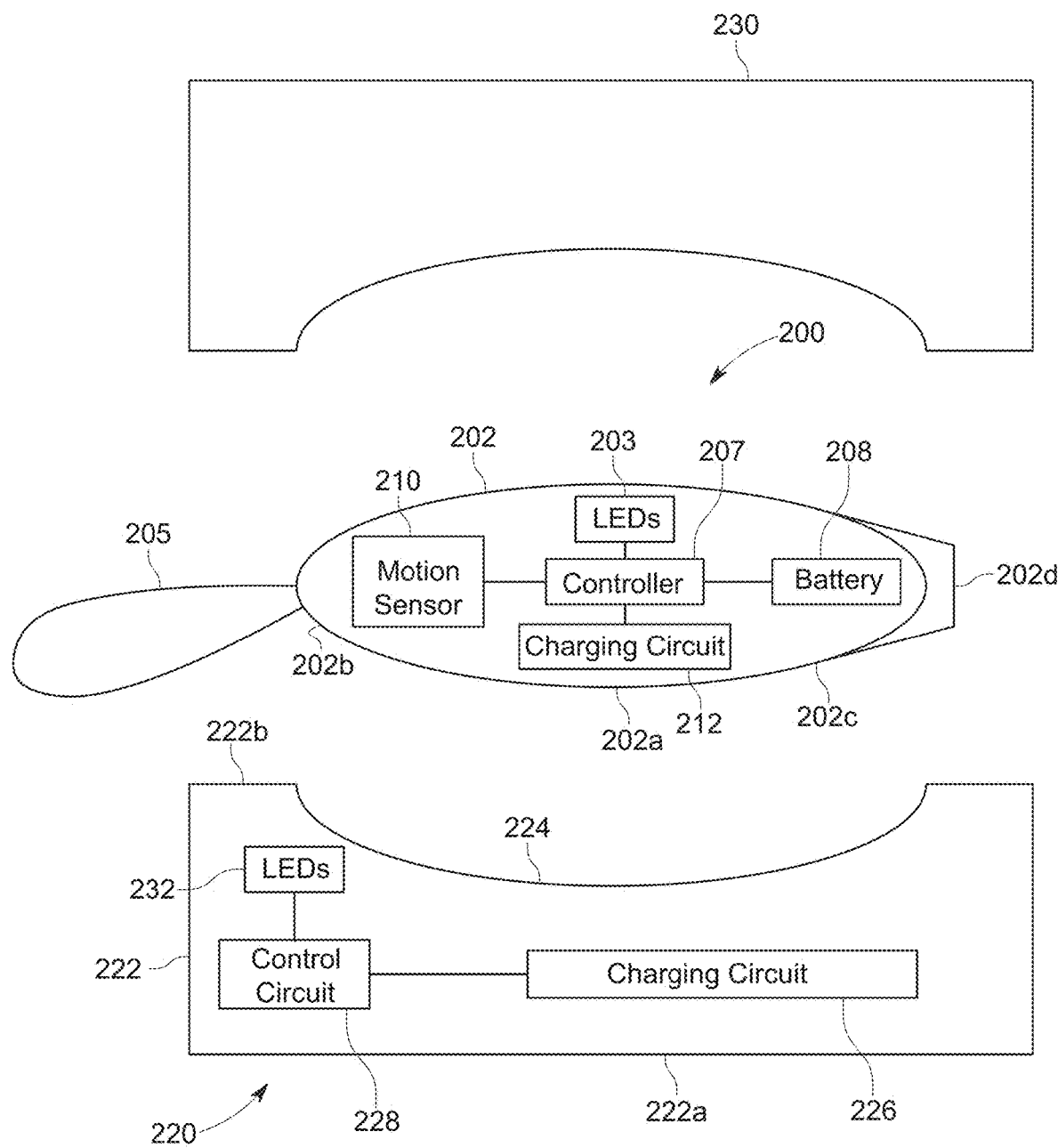
FIG. 3 is a cross-sectional view of an exemplary embodiment of a cradle for storing, charging, and/or otherwise receiving a light therapy device, such as the device shown in FIGS. 1A-1F showing exemplary components of a light therapy device and cradle.

Turning to FIGS. 3 and 4, another embodiment of a light therapy device 200 is shown that is constructed generally similar to the previous embodiments, e.g., including an oblong-shaped body 202 containing internal components of the device 200 within a sealed environment and a flexible tether 205 extending from one end of the body 202. Similar to other embodiments herein, the body 202 may include a central region 202a defining a maximum diameter that tapers to proximal and distal ends 202b, 202c. As shown, the proximal end 202b is rounded while the distal end 202c includes a cervix support surface 202d, e.g., having a flat shape as shown, or a concave, convex, or other shape (not shown) that may facilitate placement of the body 202 within a vagina against the cervix (not shown).

Generally, the device 200 includes one or more light sources, e.g., one or more LEDs 203, a controller 207, and a battery 208, similar to the previous embodiments. In addition, the device 200 includes an accelerometer or other motion sensor 210 within the body 202 that is coupled to the controller 207 instead of an external switch. For example, the controller 207 may monitor signals from the motion sensor 210 to identify predetermined commands, e.g., to activate or deactivate the LEDs 203, and/or direct the device 200 through one or more operational modes. Exemplary motions may include moving the body back-and-forth in a linear motion, spinning the body, and the like. In one embodiment, a first distinct motion or set of motions may be identified by the controller 207 to toggle the device 200, i.e., alternately activating and deactivating the LEDs 203. A second distinct motion or set of motions may be identified to direct the controller 207 to modify the activation between a menu of options, e.g., between continuous and one or more pulsed activation profiles, changing light frequency transmitted by the one or more light sources, and the like. Thus, each time the second motion is repeated, the controller 207 may modify operation of the LEDs 203 between the sequence of options. Alternatively, a distinct motion may be assigned to each desired command.

In addition or alternatively, the device 200 may include an inductive charging circuit 212 within the body 202, e.g., coupled to the battery 208. In an exemplary embodiment, the charging circuit 212 may include one or more magnets, coils, capacitors, and/or other components (not shown) that may be activated by an external magnetic field to generate electrical current to charge the battery 208, as described further elsewhere herein.

As shown in FIGS. 3 and 4, a cradle or case 220 may be provided for storing a light therapy device, such as device 200, when not in use, e.g., as part of a system or kit that may be provided to users. Generally, the cradle 220 includes a housing or base 222 and, optionally, a lid, cover, or other enclosure 230. The base 222 generally includes a planar lower surface 222a for placing the cradle 220 on a table or other surface (not shown), and an upper surface 222b including a cavity 224 sized to receive the device 200. For example, the cavity 224 may define a portion of the oblong shape of the body 202 of the device 200 such that the device 200 may be received at least partially in the cradle 220, e.g., in a predetermined orientation. In one embodiment, the cavity 224 may have an elongated oblong shape, e.g., sized to receive the body 202 sideways such that the proximal and distal ends 202b, 202c of the body 202 are positioned at opposite ends of the cavity 224, as shown in FIGS. 3 and 4. Alternatively, the cavity 224 may have a tapered side wall terminating at a flat, concave, or convex lower surface (not shown), e.g., corresponding to the shape of the cervix support surface 202d of the body 202, such that the device 200 can only be received in the cradle 220 with the cervix support surface 202d inserted first into the cavity 224. Alternatively, the cavity 224 may have other shapes, e.g., a semi- or partial-spherical or other shape (not shown) larger than the maximum dimension of the body 202 such that the device 200 may be placed in the cradle 220 in any orientation.

Figure 5A:
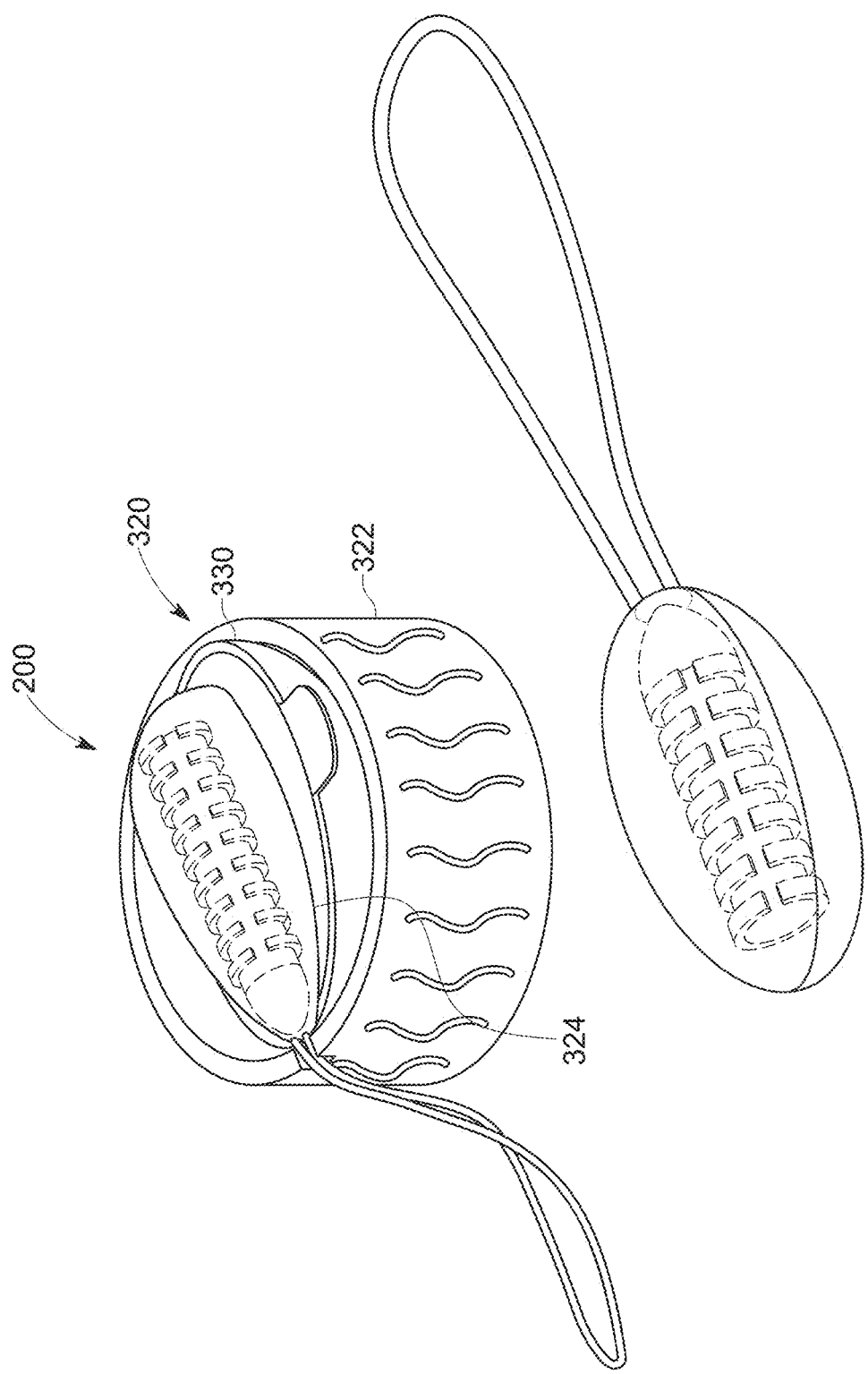
FIGS. 5A and 5B are perspective view of another embodiment of a cradle showing a lid of the cradle open and closed, respectively.
Figure 5B:
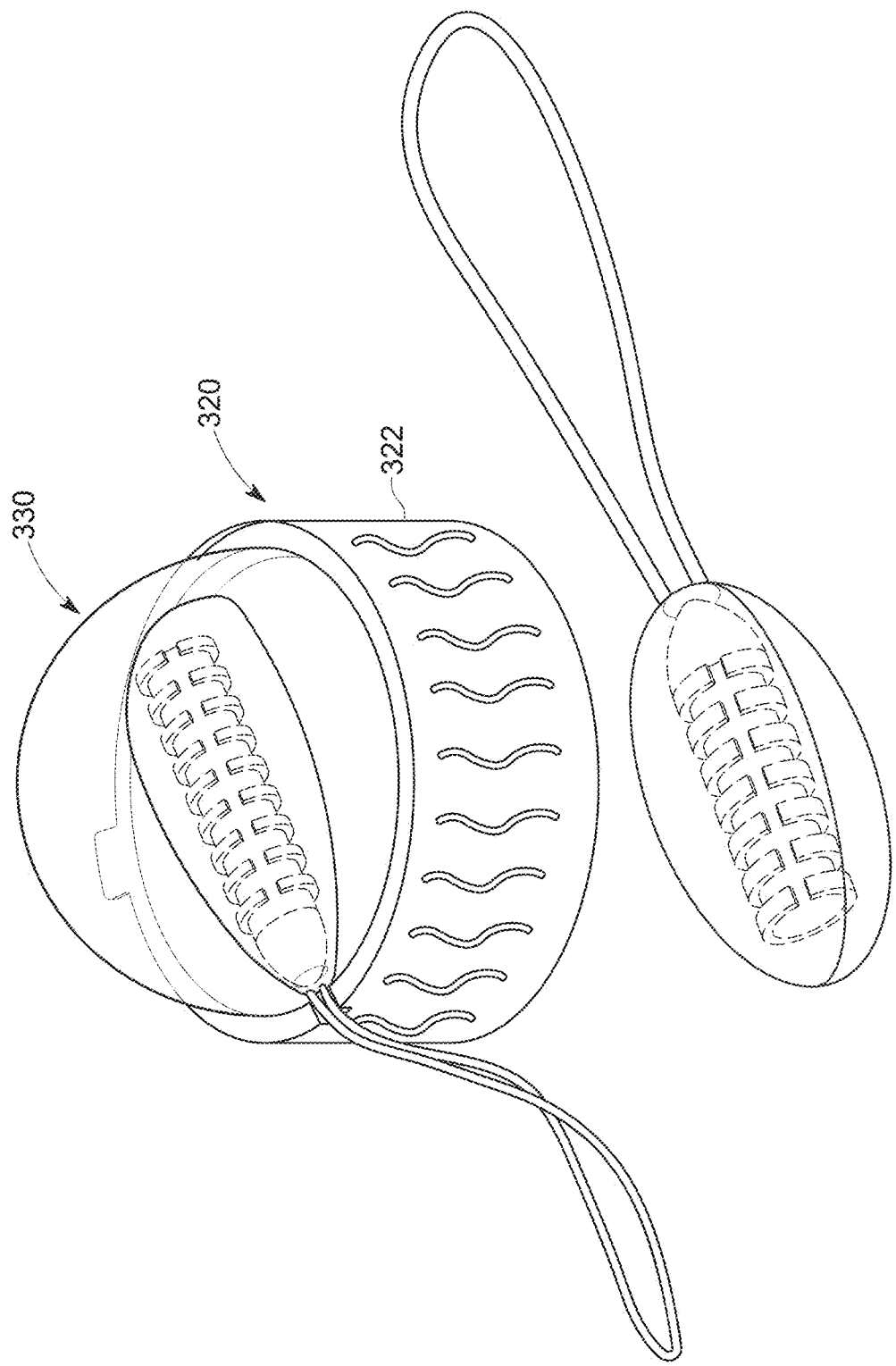

Additional embodiments of cradles are shown in FIGS. 5 and 6. For example, FIGS. 5A and 5B show a cradle 320 including a base 322 having a cavity 324 for receiving a light treatment device 200, and a lid 330 that rotatably slides into the base 322 to allow the deice 200 to be placed into and/or removed from the cavity 324. FIGS. 6A and 6B show yet another embodiment of a cradle 420 including a base 422 and a pair of clamshells or other housing members 430a, 430b that may open and close to receive a light treatment device 200 within a cavity defined by the clamshells 430a, 430b.

Returning to FIGS. 3 and 4, if the cradle 220 includes a lid 230, the lid 230 may include a cavity 232 corresponding to the cavity 224 within the base 222, e.g., to provide an enclosed chamber when the lid 230 is closed over the housing 222. The lid 230 may be coupled to the base 222 by one or more hinges (not shown), e.g., such that the lid 230 may be pivoted between open and closed positions. Alternatively, the lid 230 may be separate from the base 222 and one or more cooperating connectors, e.g., tabs, detents, grooves, and the like (not shown), may be provided that allow the lid 230 to be removably secured over the base 222 to enclose the chamber.

Optionally, the cradle 200 may include one or more features for interacting with the device 200, e.g., as shown in FIG. 3. For example, the cradle 220 may include an inductive charging circuit 226 mounted adjacent the cavity 224 for delivering energy to the charging circuit 212 of a device 200 placed in the cavity 224. For example, the charging circuit 226 may be configured to generate a magnetic field that activates the charging circuit 212 within the device 200, e.g., including one or more magnets, coils, or other components (not shown), to charge a battery of the device.

In one embodiment, the cradle charging circuit 226 may be activated automatically when the device 200 is placed in the cradle 220 or may be selectively activated by the user, e.g., by actuating a switch, button, or other actuator (not shown). For example, the cradle 220 may include a control circuit 228 that periodically activates the cradle charging circuit and identifies when the resulting magnetic field indicates that a device 200 is present in the cavity 224. Once a device 200 is identified, the control circuit 228 may activate the cradle charging circuit 226 for a predetermined time to charge the battery 208 of the device 200.

Alternatively, the controller 207 in the device 200 may include a circuit component (not shown) that modifies the magnetic field or otherwise communicates wirelessly to the cradle control circuit 228 when the controller 207 confirms that the battery 208 has been fully charged. When the cradle control circuit 228 detects the modified magnetic field or other communication from the device controller 207, the control circuit 228 may deactivate the cradle charging circuit 226.

Optionally, the cradle 220 may include one or more features to assist and/or facilitate cleaning a device 200 between uses, e.g., in addition to or instead of the inductive charging circuit 226. For example, as shown in FIG. 3, one or more light sources 232 may be provided on or in the cradle 220 for cleaning the device 200, e.g., applying anti-germicidal light at one or more frequency ranges, such as ultraviolet light, or non-ultraviolet germicidal light, and/or otherwise neutralizing latent pathogens on the outer surface of the body 202. In one embodiment where the cradle 220 includes a lid 230, the device 200 may be inserted into the cavity and the lid 230 closed to activate the light source(s) 232 to treat the device 200. For example, the cradle 220 may include a sensor (not shown) coupled to the control circuit 228 to detect when the lid 230 is closed (and a device 200 is located within the cavity 224). When the control circuit 228 confirms that the lid 230 is closed, the control circuit 228 may automatically activate the light source(s) 232, e.g., for a predetermined period of time to treat the device 200. Optionally, the cradle 220 may include a locking mechanism (not shown) that automatically locks the lid 230 once closed, e.g., until the predetermined period of time has passed to ensure that the device 200 has been sufficiently cleaned and/or to prevent inadvertent exposure to the light transmitted by light source(s) 232.

In another embodiment, a light treatment device and cradle may include a magnetic switch or other activation circuit that automatically activates the device upon removal from the cradle. For example, the cradle may include a circuit that generates a magnetic field or other energy, and the device may include a sensor therein that detects the presence and/or absence of the field/energy. Thus, when the device is removed from the cradle, the controller of the device may detect the removal and automatically activate the LEDs, e.g., immediately or after a predetermined time delay. Such a time delay may allow sufficient time to insert the device and/or may allow the controller to confirm whether the device has been placed back into the cradle within the predetermined time, e.g., to prevent accidental activation if the device falls out of the cradle and the like.

In still another embodiment, a device having a motion sensor may be used to activate the device. For example, if the controller detects lack of motion from the motion sensor for a predetermined time threshold, the controller may conclude that the device is in the cradle or otherwise not being used. Once motion is detected, the controller may automatically activate the LEDs, e.g., immediately or after a predetermined delay.

According to an embodiment herein, the device may be useful for the treatment of fungal and bacterial vaginitis, chlamydia, and/or other conditions. In case of bacterial vaginitis, there is no need for the use of additional photo sensitizing agents as bacteria are negatively affected by the light based therapy of the device 100.

The device 100 may help to eliminate or reduce undesirable microorganisms as an adjunct and forms a basis for the replacement of traditional therapies. The device 100 may also be useful for patients who are interested in non-drug therapies. The patients who cannot tolerate oral or topical azole therapy, as well as immune-compromised patients with recurrent yeast or bacterial infections can be treated with the device 100.

According to one embodiment herein, the device may be useful against fungal as well as bacterial infections. The fungal infection comprises the infection caused by yeast and especially by *Candida albicans* while the bacterial infection comprises the infection caused principally by *Gardnerella*. The patient has to determine first whether he is suffering from a fungal infection or a bacterial infection. This can be determined first through a doctor's test.

According to an exemplary embodiment, the device may be sold along with a testing strip, e.g., as part of a kit or system for treatment. The testing strip may be used for the determination of the fungal and the bacterial infection suffered by a patient according to the embodiments herein. The bacterial as well as fungal infections may be treated using the device 100 as an alternative to drugs, douches or chemicals prescribed by a doctor.

According to another embodiment, in case of fungal infection, the device may be used along with a photo-sensitizer. The photo-sensitizer may be beneficial in cases of yeast infection. The photo sensitizer comprises porfimer sodium (Photofrin), 5-aminolevulinic acid or ALA (Levulan), and methyl aminolevulinate [MAOP] (Metvix).

According to another exemplary embodiment, the device 100 may provide a low power long duration therapy so as to be safer for the mucosal tissue. The idea is that the device can be inserted overnight and removed in the morning, i.e., after several hours. The LEDs are single color or multi-color LEDs, pulsed or non-pulsed lights.

In an exemplary embodiment, the device 100 may be configured for multiple usages, e.g., such that the device 100 may be cleaned and inserted into the vagina multiple times, e.g., over several days or other course of treatment. Alternatively, the device 100 may be a single-use device, i.e., that may be discarded after being used for one treatment.

For multiple usages, the device 100 may include a rechargeable battery and a cord, which may facilitate the removal of the device from the vagina as well as acts as a connection with a suitable power source in order to recharge the device.

According to one embodiment herein, the light therapy device comprises one or more LEDs as light source for impending light on the vaginal walls. The device further comprises a battery housed inside the 100% sealed housing or the LED body. The battery may be connected to and act as a power source to the controller as well as the LEDs. The microchip controls a duration of the light therapy. A printed circuit or a suitable electronic circuitry or hub may be provided in the device for interconnecting the switch, the LEDs, the microchip and the battery. The device further comprises switch activates a device to start the light therapy. The device also comprises a tether for retrieval of the device during a light therapy. The tether is suitably replaced by a USB cord or a charging cord for making device suitable for multiple usage.

According to the embodiments herein, the device may be useful to kill or render inert the targeted species which keeps the species from replicating. The device may also be used as an adjunct therapy with existing known treatments possibly allowing for a reduction in drug or chemical based therapies. If the device is used with the conventional therapies then the device is likely to reduce the treatment times.

Thus, the device may provide a non-drug based alternative therapy based on safe and germicidal light which when introduced into the region provides a safe and effective method to treat and control both Yeast and Bacterial infection. In some applications, the device effectiveness may be enhanced through the use of a photo-sensitizer. For example, a photo-sensitizer may be applied to the outer surface of the body 102 or into pockets or features (not shown) configured for receiving the photo-sensitizer. Alternatively, the photo-sensitizer may be introduced separately into the vagina, e.g., using known applicators (not shown). The device may be used in conjunction with standard systemic drug or topical cream based therapies to lessen the duration of the event.

It is to be understood that the phraseology or terminology employed herein is for the purpose of description and not of limitation. Therefore, while the embodiments herein have been described in terms of exemplary embodiments, those skilled in the art will recognize that the embodiments herein can be practiced with modification within the scope of the claims.

I claim:

1. A method for vaginal light therapy of a patient, comprising:

providing a treatment device comprising a body having an ellipsoid shape defining a relatively large diameter central region between a proximal end and a distal end of the body, a tapered proximal region comprising a proximal surface region that tapers inwardly from the central region proximally towards the proximal end, and a tapered distal region comprising a distal surface region that tapers inwardly from the central region distally towards the distal end;

inserting the treatment device into a vagina such that the distal end of the body is disposed adjacent a vaginal cervix and the proximal end of the body is disposed within the vagina beyond an entrance to the vagina and a tether extends from the proximal end of the body exits the vagina;

activating one or more light sources carried by the body, each light source emitting light outwardly from the body at one or more wavelengths to treat fungal or bacterial vaginitis; and removing the treatment device from the vagina using the tether.

2. The method of claim 1, wherein activating the one or more light sources comprises moving the body in a predetermined sequence of movements before inserting the treatment device into the vagina.

3. The method of claim 1, further comprising, after removing the treatment device from the vagina, placing the body in a cradle to recharge a battery of the treatment device.

4. The method of claim 1, further comprising, after removing the treatment device from the vagina, placing the body in a cradle, the cradle comprising one or more light sources that are activated to clean or disinfect the treatment device before another treatment.

5. The method of claim 1, wherein inserting the device comprises:

mounting the device on a distal end of an insertion tool;

introducing the device and distal end of the insertion tool into the vagina; and once the device is positioned adjacent the vaginal cervix, removing the insertion tool.

6. The method of claim 1, wherein the tether is a cord for coupling to a power source.

7. A method for vaginal light therapy of a patient, comprising:

providing a treatment device comprising a body having an ellipsoid shape defining a relatively large diameter central region between a proximal end and a distal end of the body, a tapered proximal region tapering inwardly from the central region towards the proximal end, and a tapered distal region tapering inwardly from the central region towards the distal end;

inserting the treatment device into a vagina such that the distal end of the body is disposed adjacent a vaginal cervix and the proximal end of the body is disposed adjacent an entrance to the vagina;

activating one or more light sources carried by the body, each light source emitting light outwardly from the body at one or more wavelengths to treat one or more conditions; and removing the treatment device from the vagina.

8. The method of claim 7, wherein, when the treatment device is inserted into the vagina, a cord extends from the proximal end of the body and exits the vagina.

9. The method of claim 8, wherein the cord includes a USB connector configured for connection with a power source in order to recharge the device.

10. The method of claim 7, wherein the body defines an outer surface extending between proximal and distal ends and a cervix support surface on the distal end, and wherein the one or more light sources comprise a plurality of light sources on the outer surface with no light sources on the cervix support surface.

11. The method of claim 7, wherein the one or more light sources emit light at one or more wavelengths within a range of non-UV germicidal light.

12. The method of claim 7, wherein the one or more lights remain active for a predetermined time period upon activation whereupon the one or more lights are automatically deactivated.

13. The method of claim 7, wherein the one or more light sources are activated by a switch.

14. The method of claim 7, wherein activating the one or more light sources comprises moving the body in a predetermined sequence of movements before inserting the treatment device into the vagina.

15. The method of claim 7, further comprising, after removing the treatment device from the vagina, placing the body in a cradle to recharge a battery of the treatment device.

16. The method of claim 15, wherein a capacity of the battery is selected to limit a maximum time period during which the device may be activated or to require a minimum recharge time.

17. The method of claim 7, wherein the one or more conditions comprise fungal or bacterial vaginitis or *chlamydia*.

18. The method of claim 7, wherein the central region defines a maximum diameter for the body, and wherein the proximal and distal ends are smaller than the maximum diameter.

* * * * *